United States Patent
Pfeiffer

[11] Patent Number: 6,049,584
[45] Date of Patent: Apr. 11, 2000

[54] X-RAY DIAGNOSTIC APPARATUS FOR PRODUCING PANORAMA SLICE EXPOSURE OF BODY PARTS OF A PATIENT

[75] Inventor: Joachim Pfeiffer, Bensheim, Germany

[73] Assignee: Sirona Dental Systems GmbH & Co. KG, Bensheim, Germany

[21] Appl. No.: 09/128,097

[22] Filed: Aug. 3, 1998

[30]     Foreign Application Priority Data

Aug. 1, 1997  [DE]  Germany ........................... 197 33 338

[51] Int. Cl.$^7$ ....................................... A61B 6/14
[52] U.S. Cl. ............................. 378/39; 378/22; 378/98.8
[58] Field of Search .................................. 378/21, 22, 38, 378/39, 40, 98.8, 146; 250/370.09

[56]               References Cited

U.S. PATENT DOCUMENTS

| | | | |
|---|---|---|---|
| 4,383,327 | 5/1983 | Kruger | 378/22 |
| 4,901,337 | 2/1990 | Fujimoto | 378/98.8 |
| 4,991,192 | 2/1991 | Nishiki | 378/98.8 |
| 5,187,584 | 2/1993 | Nishiki et al. | 378/98.8 |
| 5,214,686 | 5/1993 | Webber . | |
| 5,511,106 | 4/1996 | Doebert et al. . | |
| 5,528,645 | 6/1996 | Koivisto | 378/37 |
| 5,579,366 | 11/1996 | Doebert et al. . | |
| 5,664,001 | 9/1997 | Tachibana et al. | 378/98.8 |
| 5,677,940 | 10/1997 | Suzuki et al. | 378/38 |
| 5,784,429 | 7/1998 | Arai . | |
| 5,848,123 | 12/1998 | Strommer | 378/98.8 |
| 5,917,881 | 6/1999 | Jeffery | 378/98.8 |

FOREIGN PATENT DOCUMENTS 196 51 722  12/1995  Germany .

*Primary Examiner*—David P. Porta
*Attorney, Agent, or Firm*—Hill & Simpson

[57]               ABSTRACT

An X-ray diagnostic apparatus for the production of panorama slice exposures of body parts of a patient, has a rotating unit with a source of radiation and, arranged diametrically thereto, a detector camera with a radiation-sensitive CCD detector and an image-processing unit with a computer, as well as a reproduction unit. For the subsequent determination of a sharp slice and/or of the depth of field, the CCD detector is formed by a number of narrow TDI zones with clock-out columns. The image signals corresponding to the image information containing charge packets are read out from the respective individual TDI zones, and are subject to calculations in the image processing unit, so that the depth of field of a selected slice position can be determined by modifying the local displacement of the individual images using an input unit that interacts with the image processing unit.

7 Claims, 2 Drawing Sheets

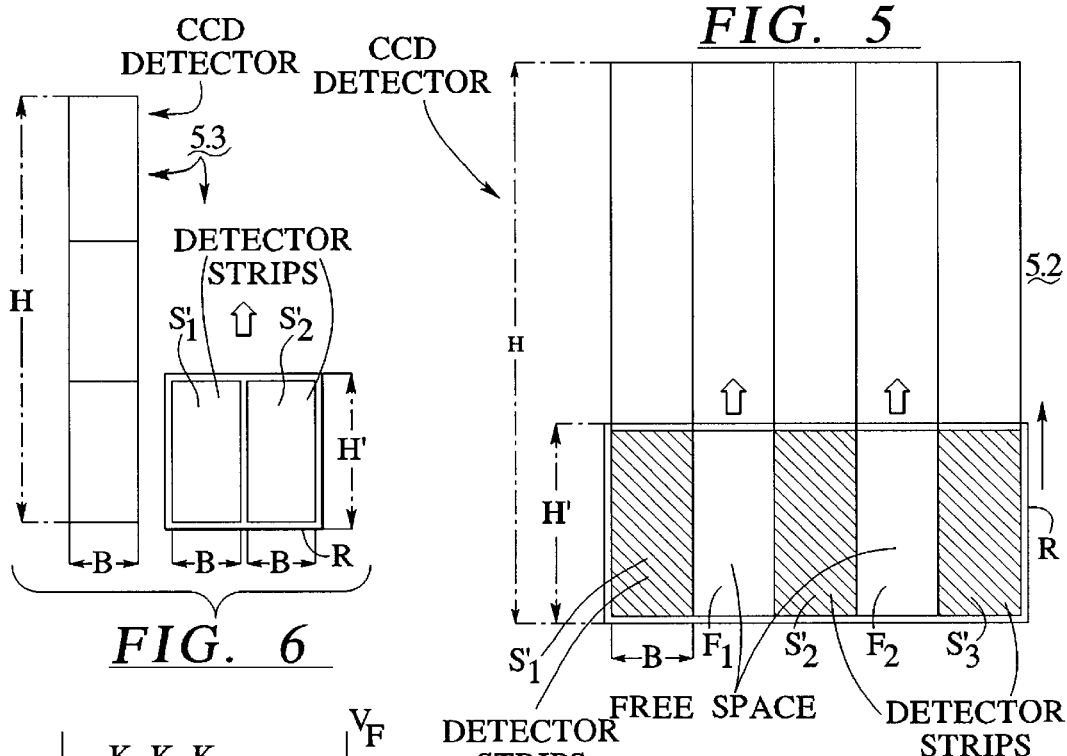
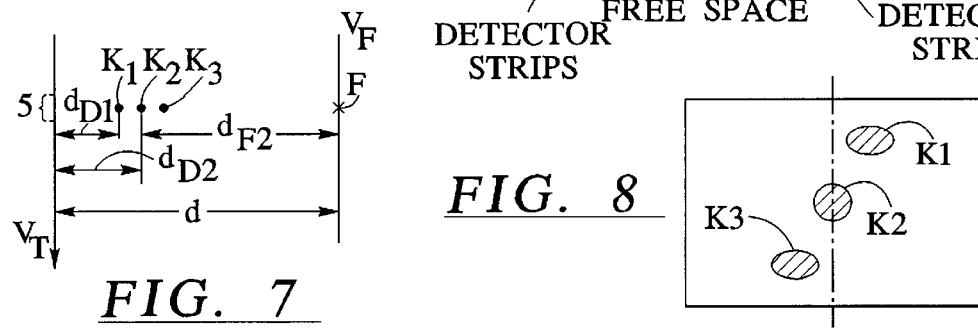
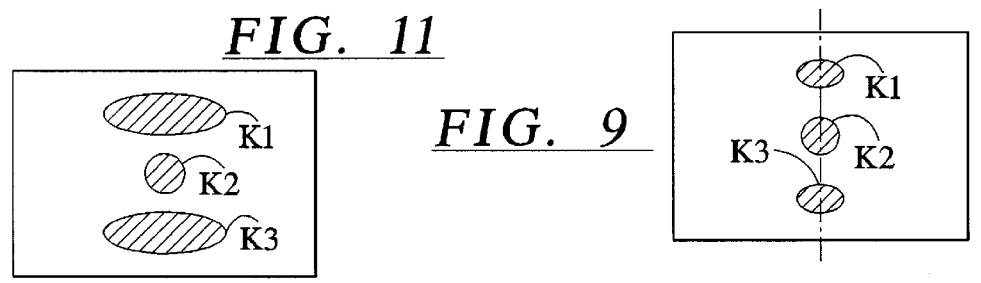
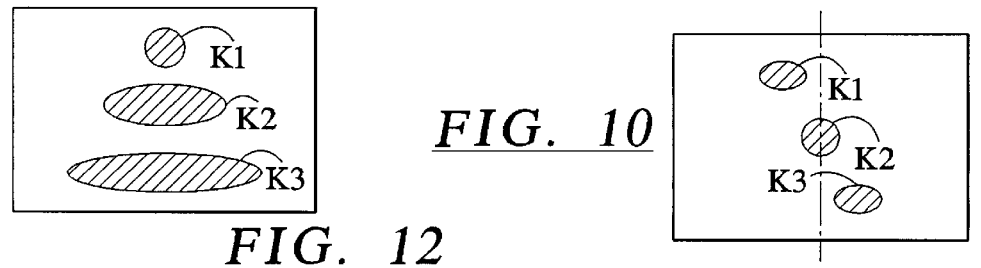

X-RAY DIAGNOSTIC APPARATUS FOR PRODUCING PANORAMA SLICE EXPOSURE OF BODY PARTS OF A PATIENT

BACKGROUND OF THE INVENTION

1. Field of the Invention

The present invention is directed to an X-ray diagnostic apparatus of the type suitable for producing panorama slice exposures of body parts of a patient, and in particular to such an x-ray diagnostic apparatus for producing panorama slice exposures of the jaw and/or teeth of a patient.

2. Description of the Prior Art

An X-ray diagnostic apparatus of the type is described, for example in European Applications 0 632 994 and 0 634 671. The detector camera in this apparatus us a one-part or multi-part X-ray beam detector of a particular height and width adapted to the object (jaw/tooth) to be photographed. A CCD sensor is provided as the detector, which, as is known, has an image zone in whose last pixel column a clock-out register is arranged.

With such a detector construction, it is not possible subsequently, i.e., after the scanning the subject to be photographed, to generate different slice positions with sufficiently good image quality; i.e., in known systems the depth of field of a subject cannot be varied far enough so that arbitrarily selectable slices can be subsequently reproduced sharply.

SUMMARY OF THE INVENTION

It is an object of the present invention to provide an X-ray diagnostic apparatus of the type described above wherein it is practical subsequently to produce and sharply image several arbitrarily selectable slices, using a single mechanically executed orthopantomogram.

The above object is achieved in accordance with the principles of the present invention in an X-ray diagnostic apparatus for producing panorama slice exposures of body parts of a patient, having a rotatable unit carrying a source of penetrating radiation and, diametrically thereto, a detector camera with a radiation-sensitive CCD detector, and having an image processing unit with a computer and a display unit, wherein, for subsequent determination of the sharp slice and/or of the depth of field, the CCD detector is formed of a number of narrow TDI zones which clock-out columns, the image information-containing charge packets being read out from the respective TDI zones individually, and the electrical signals corresponding thereto being supplied to the image processing unit, wherein the slice position is determined by modifying the local offset of the individual images, using an input unit which interacts with the image processing unit.

With the inventive X-ray diagnostic apparatus, it is possible, given an orthopantomogram produced once, to subsequently display an arbitrarily selectable slice sharply for a particular selected image segment. It is thus possible to vary the depth of field, and to vary the position of the sharp plane, especially given low depth of field, i.e. a high degree of blurring. This is also possible for images known as transverse sections. Segment-by-segment control is also possible; i.e., if for example only a partial subject, e.g. a front tooth, is of interest, the depth of field can be optimally set to this region.

The detector can be formed by several TDI zones arranged in parallel and with a spacing relative to one another, the TDI images being subsequently calculated in the computer.

The detector can alternatively be formed from TDI zones that correspond to only a part of the length of the subject to be photographed. It is also possible to construct the detector so that it contains a first group of TDI zones with a length corresponding to the image height of the subject to be photographed and, arranged adjacent thereto, at least one additional group of shorter TDI zones arranged so as to be displaceable up to the image height of the first TDI zone.

DESCRIPTION OF THE DRAWINGS

FIG. 5 shows a second variant of the embodiment according to FIG. 3.

FIG. 6 shows a third variant of the embodiment according to FIG. 3.

FIG. 7 schematically illustrates geometrical relationships of various parameters for explaining the subject matter of the invention.

FIGS. 8 through 10 respective show images of respective, individual TDI zones obtained in accordance with the invention.

FIG. 11 shows a summation image produced by selecting, via an input unit, a subject point $K_2$ as always being at the same location.

FIG. 12 shows a summation image produced by selecting, via an input unit, a subject point $K_1$ as always being at the same location.

DESCRIPTION OF THE PREFERRED EMBODIMENTS

Figure 1:
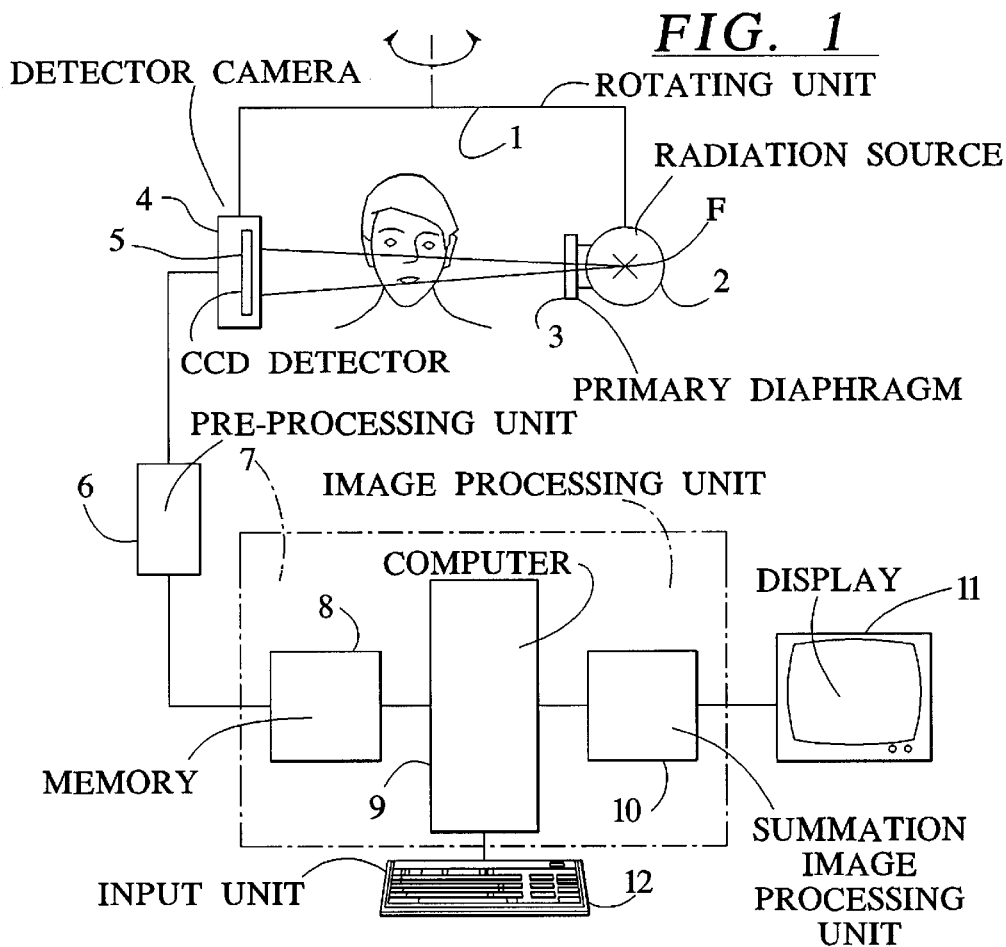
FIG. 1 is a schematic diagram of the inventive X-ray diagnostic apparatus.

On the basis of FIG. 1, the general construction of the X-ray diagnostic apparatus and the procedural steps for the production of a panorama slice exposure (orthopantomogram) are explained.

A rotating unit 1 that can be pivoted about a patient's head (not shown in more detail) supports, in a known way, a radiation source 2 with a primary diaphragm 3 and, diametrically opposite, a detector camera 4 with a CCD detector 5. The X-ray beam emanating from the focus F of the radiation source 2 is limited by the primary diaphragm 3 and a secondary diaphragm (not shown in more detail) in the region of the CCD detector 5. The image signals generated by the CCD detector 5 are supplied to a pre-processing unit 6, in which they are compressed. For the compression, a similarity comparison between the signals of the clock-out register of the TDI zones in the subsequent image processing unit 7 can, for example, be used, with only the difference signals being reproduced. The amount of data to be transmitted can thereby be reduced.

The image processing unit 7 has a digital memory 8 in which the individual images are stored, or are intermediately stored, a computer 9 and a summation image production unit 10. A display 11 and an input unit 12 are connected to the image processing unit 7. By means of the input unit 12, among other things it is possible for the user to modify the local displacement, which is discussed in more detail below.

Before explaining the inventive detector in more detail, it will be useful to briefly discuss a detector arrangement as provided in apparatuses according to the prior art. As an example, the following description is based on a detector size with a width (B) of 5 mm and a height (H) of 150 mm. Such a detector size is today conventionally provided for the production of panorama X-ray exposures in the jaw or tooth region.

Figures 2, 3, 4:
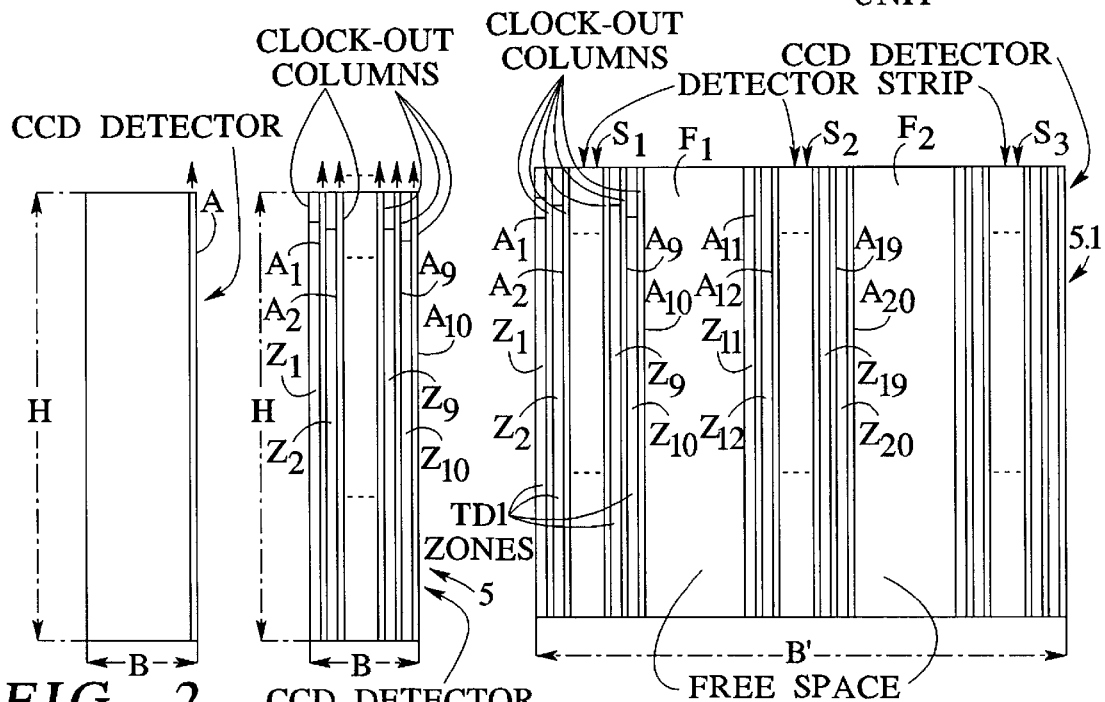
FIG. 2 shows the design of a detector according to the prior art.
FIG. 3 shows the design of the inventive detector.
FIG. 4 shows a first variant of the embodiment according to FIG. 3.

The detector according to FIG. 2 is a CCD with, typically, 100 pixels per line. On one edge, i.e. close to the active image zone, there is conventionally a clock-out column, designated in general with A. The image signals (i.e., the image information-containing charge packets) generated in the CCD image zone are read out in the TDI mode, and are correspondingly processed in the subsequent image processing unit. The readout in the TDI mode and the image processing are described in more detail in European Application 0 279 294.

In FIG. 3, the inventive detector 5 is shown in a first variant, whereby for comparison with a detector according to the prior art the same detector dimensions (5×150 mm) are assumed.

The inventive detector is divided into a number (here ten) of 500μm-wide TDI zones, with a clock-out column adjacent to each TDI zone. Each TDI zone contains about 10 50-μm pixels, and the clock-out column is subsequently adjacent. In FIG. 3, the individual TDI zones are designated Z and the clock-out columns are designated A. For the selected embodiment, with a detector width of 5 mm, ten TDI zones (Z1 to Z10) result, with a corresponding number of clock-out columns (A1 to A10).

The selected number of TDI zones results from the desired minimal depth of field, or from a minimally required CCD detector width. The width of a TDI zone is determined by the transmission width of the system according to the CCD, the sensitivity of the detector and the desired resolution of the system. In the present embodiment, the ten TDI zones would result in a depth of field or slice thickness of approximately 1 to 2 mm.

If warranted, the output of the ten TDI zones can be partially serialized on the CCD chip, according to which data transmission is desired on a line, or how many data lines can be maintained in parallel up to the digitization. All the data corresponding to the output of the ten TDI zones are compressed in the pre-processing unit 6, and are subsequently stored in the memory 8.

Before the image generation and subsequent selection of a slice are explained, three variants of the inventive detector are shown.

FIG. 4 shows a variant in which the overall detector 5.1 is wider than the one shown in FIG. 3, and the detector is alternatively fashioned from CCD chips arranged parallel to one another, corresponding to the manner shown in FIG. 3, with free spaces $F_1$, $F_2$ lying therebetween. The overall detector thus has five strips, each having a width of 5 mm. The overall width B' is thus 25 mm. After a first strip $S_1$ with ten TDI zones ($Z_1$ to $Z_{10}$) there follows a free space $F_1$ (without a TDI zone), likewise of 5 mm width, and after this there is again a strip ($S_2$) with ten TDI zones ($Z_{11}$ to $Z_{20}$), etc. Wide detectors constructed in this way make it possible to produce images with low depth of field. This is of interest in particular in combination with the possibility of determining the position of the sharp slice by calculation after the exposure. The described arrangement with free (open) spaces produces images whose image quality is only insignificantly worse than an arrangement in which the entire surface is constructed as a sensitive surface. However, the described arrangement has cost advantages, and functions with a lower dose load.

In the arrangement described above, it is assumed that the blurring effect that arises in an X-ray exposure results from superposition of the individual images produced by the strips S1 to S3, with local displacement corresponding to the desired slice. As long as the structures to be blurred and the blurring width are sufficiently large, in a detector constructed in this way the overall image is not significantly different than in a detector in which the free spaces $F_1$, $F_2$, . . . are likewise occupied with TDI zones. Calculations for this embodiment have yielded the result that free spaces of 5 mm are acceptable.

In order to avoid unnecessary irradiation of the patient, in this variant the primary diaphragm 3 is constructed as a strip-type raster diaphragm, so that the edges and free spaces of the detector are screened from the radiation.

FIG. 5 shows a further variant of a detector arrangement (5.2), in which the chip height H' of the three TDI strips $S_1'$, $S_2'$ and $S_3'$ is only ⅓ of the detector height H of the previously described embodiment. The three CCD chips are arranged on a frame R, which is arranged in a displacement mount (not shown in more detail) so as to be displaceable in the direction of the arrow.

FIG. 6 shows a detector arrangement 5.3 in which a first (three-part) CCD chip with a width B of about 5 to 8 mm and a height H of 150 mm is provided, and in which two additional chips with dimensions B×H' as previously described, thus approximately 5×50 mm, are arranged in displaceable fashion with a lateral spacing of 5 mm. The displacement mount is provided with defined snap positions that correspond to snap positions of the primary diaphragm 3. Such a combination solution is particularly advantageous because the greater blurring effect (lower depth of field) enabled by the additional chips is generally required only in a certain segment of a panorama exposure.

The following provides an explanation of the blurring effect, as well as describing the slice selection that can be carried out subsequently, in the context of the example of a CCD detector according to FIG. 3. The description is also applicable in principle for the variants according to FIGS. 4 to 6.

In the depth of field discussion, for simplicity imaging is assumed to be of a sphere with a diameter of a few millimeters, as a subject to be photographed, with a width of the radiation fan or of the secondary diaphragm of 5 mm being assumed, which is a width typically used for an orthopantomogram. The classical layer exposure situation is assumed, i.e., it is assumed that the focus F of the radiation source 2 moves on a straight line, while the detector 5 remains stationary. The focus F then moves with speed $V_F$; the reading out of the image data in the detector takes place with TDI speed $V_T$. Assuming the geometry shown in FIG. 7, the following relation result, whereby:

d=distance focus–detector
$d_{F2}$=distance focus–subject point $K_2$
$d_{D2}$=distance detector–subject point $K_2$
$d_{D1}$=distance detector–subject point $K_1$ Given $V_T=V_F \cdot d_{D2}/d_{F2}$, a slice $K_2$ that proceeds through the midpoint of the sphere lies precisely in the sharp plane. The speed of $K_1$ (of a sphere outside the sharp plane) on the detector is $V_{K1D}=V_F \cdot d_{D2}/d_{F1}$. The speed in the TDI-displaced image is $V_{K1T}=V_F/d_{F2}(d_{D1}-d_{D2})=V_F/d_{F2} \cdot d_{K1K2}$.

A blurring arises as long as $K_1$ is imaged on the detector. $K_1$ travels over the detector with $V_{K1D}$, and is thus imaged thereon over the time period $t_{DK1}=b/V_{K1D}=b/V_F \cdot d_{F2}/d_{D1}$. In this time period, $K_1$ is blurred by $I_V=d_{K1K2} \cdot b/d_{D1}$ (b is the detector width).

If the sharp slice is defined as the region inside this boundary, the following holds: unsharpness caused by motion=system unsharpness ($U_S$); thus, the boundary of the sharp slice (T, depth of field) is the distance $d_{K1K2}$, where $I_V = U_S$. From this, there results: $U_S = T \cdot b/d_{D1}$ or $T = U_S/b \cdot d_{D1}$.

The above considerations support the following statements:

1) For $b = U_S$, every body is "depth-sharp" (i.e., has the proper depth of focus).

2) For $U_S/b = 1:50$, as is standard in orthopantomograms, for $d_{D1} = 50$ mm there results a depth of field T=1 mm. This statement is consonant with practical experience, since according to the above definition of depth of field this is the region in which almost no loss of resolution occurs.

3) For $U_S/b = 1:5$, as is the case for the individual TDI zones of the detector according to FIG. 3, with $d_{D1} = 50$ mm there results a depth of field region of 10 mm; since this holds for both sides, this depth of field region is sufficient to image sharply all regions of the tooth.

The following explains on the basis of FIGS. 8 to 12 how the images of the individual TDI zones of a detector according to FIG. 3, which considered individually have a very high depth of field, can be combined by means of subsequent calculating to form images with low depth of field, and the position of the sharp slice can be determined subsequently.

The images of the individual TDI zones are as shown in FIGS. 8 to 10. FIG. 8 here shows the image of zone 1, FIG. 9 shows the image of zone 5, and FIG. 10 shows the image of zone 10.

In all zones, $K_2$ is imaged sharply, while $K_1$ and $K_3$ are slightly unsharp. In the various zone images, however, the images of $K_1$, $K_2$, $K_3$ are offset differently to one another. For clarity, the unsharpness is shown in greatly exaggerated fashion.

If the images of zones 1 to 10 are summed with a displacement along the direction of blurring (local displacement), selected so that $K_2$ is always at the same location, a summation image as shown in FIG. 11 results.

If summation takes place with a displacement selected such that $K_1$ always remains at the same position, there results a summation image as shown in FIG. 12.

The same holds for $K_3$.

From the above, it is apparent that a subject ($K_1$, $K_2$ or $K_3$) can subsequently be displayed sharply according to the "local displacement."

The subsequently calculated image of $K_2$ is equivalent to an image obtained conventionally with a detector (according to FIG. 2). The subsequently calculated images of K, and $K_3$ are only slightly less sharp than that of $K_2$, corresponding to the high depth of field of the narrow TDI zones of the detector according to FIG. 3.

The subsequent variation of the slice position can, for example, be realized in such a way that, in a software-controlled dialog, the user modifies the local displacement between the individual zone images. e.g. by moving a controller indicated on the display screen. The indicated summation image is then calculated again from the individual zone images, with the local displacement modified in this way, and is displayed on the display screen.

The fact that the images of the individual TDI zones can be subsequently calculated individually can also be used to vary the depth of field of the calculated image, e.g. by not including all the TDI zones in the calculation.

Although modifications and changes may be suggested by those skilled in the art, it is the intention of the inventor to embody within the patent warranted hereon all changes and modifications as reasonably and properly come within the scope of his contribution to the art.

I claim as my invention:

1. An X-ray diagnostic apparatus for producing panorama slice exposures of body parts of a subject, comprising:

a mechanically rotatable unit carrying a source of penetrating radiation and, opposite thereto, a detector camera containing a penetrating radiation-sensitive CCD detector, said rotating unit being adapted for rotating said source of penetrating radiation and said detector camera around a subject to conduct an exposure;

said CCD detector comprising a plurality of narrow TDI zones and a plurality of clock-out columns respectively allocated to the TDI zones in said plurality of TDI zones, each TDI zone generating image signals;

said detector camera including means for individually reading out the respective image signals from the TDI zones;

an image processing unit containing a computer supplied with said image signals from the respective, individual TDI zones;

a manually operable input unit which supplies signals to said computer modifying a local offset of individual images obtained from the respective TDI zones;

said computer comprising means, after completion of said exposure, for subsequently determining at least one of a sharp slice and a depth of field with the slice position determined by the signals from the input unit and by performing calculations on said image signals from the respective TDI zones; and display means, connected to said image processing unit, for displaying an image of the slice position.

2. An X-ray diagnostic apparatus as claimed in claim 1 further comprising a preprocessing unit, to which all of the respective image signals from the plurality of TDI zones are supplied for compressing said image signals.

3. An X-ray diagnostic apparatus as claimed in claim 1 wherein said plurality of TDI zones are disposed parallel to and spaced from each other.

4. An X-ray diagnostic apparatus as claimed in claim 3 wherein CCD detector comprises a plurality of individual detector elements disposed on a carrier with free spaces between the respective detectors, said detectors respectively comprising said TDI zones.

5. An X-ray diagnostic apparatus as claimed in claim 4 wherein each of said individual detectors has a width in a range between 3 mm and 10 mm.

6. An X-ray diagnostic apparatus as claimed in claim 5 wherein each of said individual detectors has a width of approximately 5 mm.

7. An X-ray diagnostic apparatus as claimed in claim 3 wherein an image of the subject produced by said detector camera has an image height, and wherein said detector contains a first of said TDI zones having a length substantially equal to said image height, and at least one additional one of said TDI zones having a height which is less than said image height disposed next to said first TDI zone, and means for moving said at least one additional TDI zone up to said image height of said first TDI zone.

* * * * *